United States Patent

White et al.

[11] 4,073,906
[45] Feb. 14, 1978

[54] PYRIMIDO[1,2-b]ISOQUINOLINES

[75] Inventors: Alan Chapman White, Windsor; Robin Michael Black, Porton, both of England

[73] Assignee: John Wyeth & Brother Limited, Maidenhead, England

[21] Appl. No.: 629,205

[22] Filed: Nov. 5, 1975

[30] Foreign Application Priority Data

Nov. 20, 1974 United Kingdom ............... 50179/74

[51] Int. Cl.² ................... A61K 31/305; C07D 239/70
[52] U.S. Cl. ............................... 424/251; 260/251 A
[58] Field of Search .................... 260/251 A; 424/251

[56] References Cited

U.S. PATENT DOCUMENTS 3,850,957 11/1974 White et al. ................. 260/251 A X

FOREIGN PATENT DOCUMENTS 1,366,133 9/1974 United Kingdom.

Primary Examiner—Paul M. Coughlan, Jr.
Assistant Examiner—D. B. Springer

Attorney, Agent, or Firm—Arthur E. Wilfond

[57] ABSTRACT

The invention relates to pyrimido[1,2-b]isoquinolines of the formula

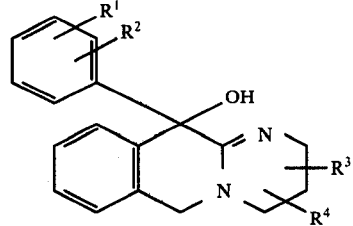

and their pharmaceutically acceptable acid addition salts. In the formula, $R^1$ and $R^2$ each represent hydrogen, hydroxyl, lower alkyl, lower alkoxy, trifluoromethyl, halogen, amino or mono- or di-(lower)alkylamino and $R^3$ and $R^4$ each represent hydrogen or lower alkyl. The compounds have utility as anti-gastric ulcer agents.

7 Claims, No Drawings

PYRIMIDO[1,2-b]ISOQUINOLINES

This invention relates to heterocyclic compounds. More particularly the invention relates to certain novel pyrimido [1,2-b]isoquinolines, to methods of preparing the novel compounds and to pharmaceutical compositions containing them.

According to the present invention there are provided pyrimido[1,2-b]isoquinolines of the general formula (I)

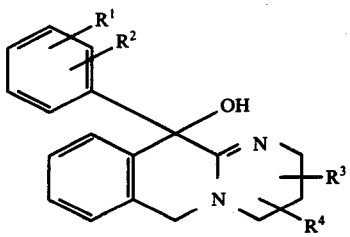

and their pharmaceutically acceptable acid addition salts. In general formula (I), $R^1$ and $R^2$ each represent hydrogen, hydroxyl, lower alkyl, lower alkoxy, trifluoromethyl, halogen, amino or mono- or di-(lower)alkylamino and $R^3$ and $R^4$ each represent hydrogen or lower alkyl.

The term "lower" as used herein means that the radical referred to contains 1 to 6 carbon atoms. Preferably the radical contains 1 to 4 carbon atoms.

The substituents $R^1$ and $R^2$ can be the same or different and they can be hydrogen, hydroxyl, lower alkyl (e.g. methyl, ethyl, propyl or butyl), lower alkoxy (e.g. methoxy, ethoxy, propoxy or butoxy), trifluoromethyl, halogen (e.g. chlorine or bromine), amino, mono(lower)alkylamino (e.g. methylamino) or di(lower)alkylamino (e.g. dimethylamino). Preferably both $R^1$ and $R^2$ are hydrogen or one is hydrogen and the other is halogen.

The substituents $R^3$ and $R^4$ can be the same or different i.e. they can both represent hydrogen, one can represent hydrogen and the other lower alkyl (e.g. methyl, ethyl, propyl or butyl) or both can represent a lower alkyl radical. When both $R^3$ and $R^4$ are lower alkyl (e.g. methyl) they can be on different carbon atoms of the pyrimido[1,2-b]isoquinoline nucleus or they can be on the same carbon atom (e.g. carbon atom 3).

The compounds of the invention may be prepared by reacting a ketone of general formula (II)

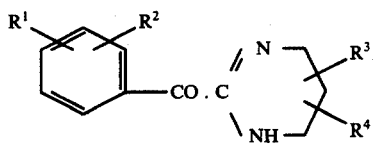

wherein $R^1$, $R^2$, $R^3$ and $R^4$ are as defined above with a Grignard reagent of general formula (III)

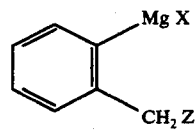

where X is a halo atom, particularly chloro or bromo, and Z is a protected hydroxy group. Z may be a protected hydroxy group which is stable in the presence of Grignard reagents. Suitable protected hydroxy groups include 2-tetrahydropyranyloxy, methoxy, trimethylsilyloxy. The reactants of general formulae (II) and (III) may be reacted together in an inert organic solvent which may be heated if required and the product of general formula (I) isolated by decomposing the reaction mixture, e.g. with ice and ammonium chloride solution.

The ketones of general formula (II) may be prepared according to the method described in our United Kingdom Patent specification No. 1,403,732. Compounds of general formula (III) are, in general, known and can be prepared by protecting the hydroxy group of an o-halobenzyl alcohol and converting the protected alcohol to the Grignard reagent by reaction with magnesium.

The compounds of the invention may also be prepared by an alternative method which comprises cyclising an alcohol of general formula (IV).

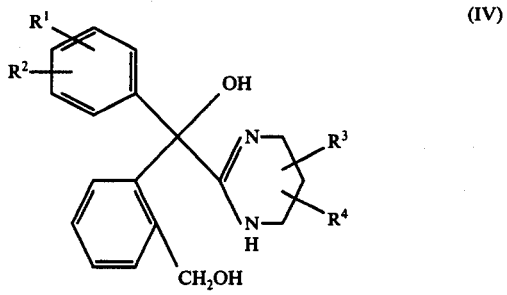

where $R^1$, $R^2$, $R^3$ and $R^4$ have the meanings given above. The alcohol of general formula (IV) may be cyclised directly by heating in an inert organic solvent or indirectly e.g. by replacing the primary hydroxyl group with halogen, e.g. by reaction with thionyl chloride, and cyclising the resulting compound of general formula (V)

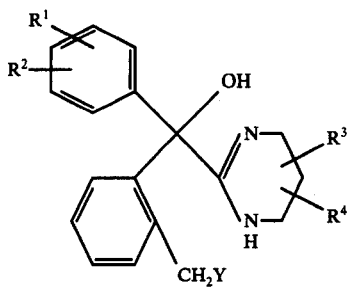

wherein $R^1$, $R^2$, $R^3$ and $R^4$ are as defined above and Y is halo under basic conditions (e.g. with an alkali metal alkoxide). The starting materials of general formula (IV) may be isolated as a by-product if, for example the compound of general formula (II) is reacted with the compound of general formula (III) at about room temperature. For example, compounds (IV) may be isolated by crystallisation of the mother liquors of the reaction medium.

If in the process described above the compound of the invention is obtained as an acid addition salt, the free base can be obtained by basifying a solution of the acid addition salt. Conversely if the product is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds. Examples of suitable acids that may be used include hydrochloric, hydrobromic, tartaric, phosphoric, maleic, citric, methanesulphonic and p-toluene sulphonic acids.

The compounds of the invention possess an asymmetric carbon atom and hence optical enamtiomorphs are possible.

The compounds of the invention may be in the form of specific optical isomers or mixtures of such isomers, such as racemates. The optical isomers may be prepared from a racemic mixture by the use of standard methods described in the literature.

The compounds of the invention have utility as anti-gastric ulcer agents as indicated by standard tests on warm blooded animals. In one such procedure the ability of the compounds to reduce gastric secretions was measured by a standard pharmacological procedure in rats (Shay et al, Gastroenterology, 1954, 26, 906 – 913). In this procedure it was found that representative compounds such as 3,4,6,11-tetrahydro-11-phenyl-2H-pyrimido[1,2-b]iosquinolin-11-ol, 11-(p-chlorophenyl)-3,4,6,11-tetrahydro-2H-pyrimido[1,2-b]isoquinolin-11-ol, 3,4,6,11-tetrahydro-3,3-dimethyl-11-phenyl-2H-pyrimido[1,2-b]isoquinolin-11-ol and 11-(m-chlorophenyl)-3,4,6,11-tetrahydro-2H-pyrimido[1,2-b]isoquinolin-11-ol were active when administered at a dosage of 30 mg/kg intraduodenally. Some of the compounds of the invention, in particular, the compound in which $R^1$, $R^2$, $R^3$ and $R^4$ are all hydrogen, possess hypoglycaemic activity as indicated by the following standard pharmological procedure. Male rats are fasted overnight, a control blood sample is then taken from the tail and the test compound is then administered at a dose of 50mg/kg by stomach tube. Subsequent blood samples are then taken at hourly intervals and the depression in blood sugar concentration relevant to the control sample is noted.

The invention further provides a pharmaceutical composition which comprises a compound of formula (I) or a pharmaceutically acceptable acid addition thereof, in association with a pharmaceutically acceptable carrier. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form. The daily dose of the compound will vary depending upon the route of administration, the particular compound employed and the particular animal involved. The daily dose for a 70 kg mammal could be, for example, within the range 25 to 1000 mg.

The following examples illustrate the invention:

EXAMPLE 1

3,4,6,11-Tetrahydro-11-phenyl-2H-pyrimido[1,2-b]isoquinolin-11-ol

A solution of phenyl 1,4,5,6-tetrahydro-2-pyrimidyl ketone (1.88 g., 0.01 mole) in dry tetrahydrofuran (25 ml.) was added dropwise to a stirred boiling solution of o-(2-tetrahydropyranyloxymethyl)phenylmagnesium bromide [made from magnesium (0.6g., 0.025 mole) and 2-(o-bromobenzyloxy)tetrahydropyran (6.78 g., 0.25 mole)] in dry tetrahydrofuran (30 ml.), the solution was heated under reflux for a further 4 hours and stirred overnight at room temperature. The solution was poured onto ice/ammonium chloride solution, extracted with chloroform and the combined extracts washed with water. After evaporation of the chloroform the residue was taken up in benzene, extracted with 2N hydrochloric acid, the combined extracts basified (NH$_4$OH) and extracted with chloroform. The extracts were washed with water, dried (MgSO$_4$) and the chloroform removed to yield a white crystalline residue. Recrystallisation from isopropanol gave the title compound (1.121 g., m.p. 133°–135° C). The hydrobromide salt of the title compound crystallised from isopropanol/ether, m.p. 244°–246° C.

Found: C, 60.25; H, 5.5; N, 7.7% $C_{18}H_{18}N_2O \cdot HBr$ requires C, 60.2; H, 5.35; N, 7.8%.

EXAMPLE 2

11-(p-chlorophenyl)-3,4,6,11-tetrahydro-2H-pyrimido-[1,2b]isoquinolin-11ol

A solution of p-chlorophenyl 1,4,5,6-tetrahydro-2-pyrimidyl ketone (2.23 g., 0.01 mole) in dry tetrahydrofuran (20 ml.) was added dropwise to a boiling solution of o-(2-tetrahydropyranyloxymethyl)phenylmagnesium bromide (0.025 mole) in dry tetrahydrofuran (30 ml.). The solution was heated under reflux for a further 4 hours and then stirred overnight at room temperature. The mixture was worked up as in Example 1 to give the title compound as a crude free base, which crystallised as needles from isopropanol (1.01 g., m.p. 98°–101° C). The hydrobromide salt of the title compound crystallised from isopropanol/ether, m.p. 219°–221° C (some decomposition).

Found: C, 54.95; H, 4.86; N, 7.0%. $C_{18}H_{17}ClN_2O$ requires C, 54.9; H, 4.6; N, 7.1%.

EXAMPLE 3

3,4,6,11-Tetrahydro-3,3-dimethyl-11-phenyl-2H-pyrimido-[1,2-b]isoquinolin-11-ol A solution of phenyl 1,4,5,6-tetrahydro-5,5-dimethyl-2-pyrimidyl ketone (1.25 g.) in dry tetrahydrofuran (10 ml.) was added dropwise to a boiling solution of o-(2-tetrahydropyranyloxymethyl)phenylmagnesium bromide [made from magnesium (0.36 g.) and 2-(o-bromobenzyloxy)tetrahydropyran (4.07 g.)] in dry tetrahydrofuran (20 ml.). The mixture was heated under reflux for a further 4 hours, stirred overnight at room temperature and worked up as in Example 1. The title compound crystallised as needles from isopropanol (0.941 g., m.p. 111°–112° C). The hydrobromide salt of the title compound crystallised from isopropanol/ether, m.p. 214°–215° C.

Found: C, 62.3; H, 6.2; N, 6.95%. $C_{20}H_{22}N_2O \cdot HBr$ requires C, 62.0; H, 6.0; N, 7.2%.

EXAMPLE 4

11-(m-chlorophenyl)-3,4,6,11-tetrahydro-2H-pyrimido-[1,2-b]isoquinolin-11-ol A solution of m-chlorophenyl 1,4,5,6-tetrahydro-2-pyrimidyl ketone (4.46 g., 0.02 mole) in dry tetrahydrofuran (30 ml.) was added dropwise to a boiling solution of o-(2-tetrahydropyranyloxymethyl)phenylmagnesium bromide (0.05 mole) in dry tetrahydrofuran (50 ml.). After heating under reflux for a further 4 hours and stirring overnight at room temperature the mixture was worked up as in Example 1. The title compound crystallised from isopropanol (3.385 g., m.p. 100°–101° C). The hydrochloride salt of the title compound crystallised from ethanol/chloroform/ether, m.p. 261°–265° C (dec.).

Found: C, 62.3; H, 5.3; N, 7.8%. $C_{18}H_{17}ClN_2O \cdot HCl$ requires C, 61.9; H, 5.2; N, 8.0%.

We claim:

1. A pyrimido[1,2-b] isoquinoline selected from the group consisting of a base of the formula

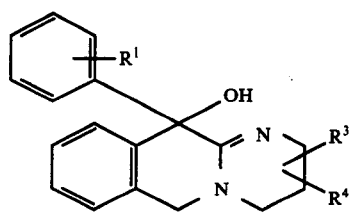

and a pharmaceutically acceptable acid addition salt thereof; wherein $R^1$ represents hydrogen, hydroxyl, lower alkyl, lower alkoxy, trifluoromethyl, or halogen; and $R^3$ and $R^4$ each represents hydrogen or lower alkyl; said lower alkoxy or lower alkyl groups having up to six carbon atoms, with the proviso that $R^3$ and $R^4$ cannot be groups which give rise to steric hindrance.

2. A compound according to claim 9 which is 3,4,6,11-tetrahydro-11-phenyl-2H-pyrimido[1,2-b]isoquinolin-11-ol or a pharmaceutically acceptable acid addition salt thereof.

3. A compound according to claim 1 which is 11-p(chlorophenyl)-3,4,6,11-tetrahydro-2H-pyrimido[1,2-b]isoquinoline-11-ol or a pharmaceutically acceptable acid addition salt thereof.

4. A compound according to claim 1 which is 3,4,6,11-tetrahydro-3,3-dimethyl-11-phenyl-2H pyrimido[1,2b]isoquinolin-11-ol or a pharmaceutically acceptable acid addition salt thereof.

5. A compound according to claim 1 which is 11-(m-chlorophenyl)-3,4,6,11-tetrahydro-2H-pyrimido[1,2-b]isoquinolin-11-ol or a pharmaceutically acceptable acid addition salt thereof.

6. A compound according to claim 1 wherein $R^1$ is hydrogen or halogen.

7. An anti-ulcer composition containing an effective amount of a pyrimido[1,2-b]isoquinoline selected from the group consisting of a base of the formula

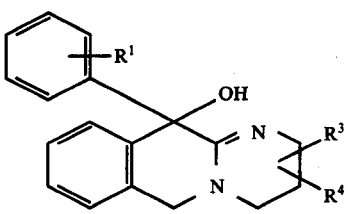

and a pharmaceutically acceptable acid addition salt thereof; wherein $R^1$ represents hydrogen, hydroxyl, lower alkyl, lower alkoxy, trifluoromethyl, or halogen; and $R^3$ and $R^4$ each represents hydrogen or lower alkyl; said lower alkoxy or lower alkyl groups having up to six carbon atoms, with the proviso and $R^3$ and $R^4$ cannot be groups which give rise to steric hindrance, and a pharmaceutically acceptable carrier.

* * * * *

UNITED STATES PATENT AND TRADEMARK OFFICE
CERTIFICATE OF CORRECTION

PATENT NO. : 4,073,906
DATED : February 14, 1978
INVENTOR(S) : Alan C. White and Robin M. Black It is certified that error appears in the above-identified patent and that said Letters Patent are hereby corrected as shown below:

Column 3, line 8, "enamtiomorphs" should read - - enantiomorphs - - ;

Claim 2, line 1, "claim 9 " should read - - claim 1 - - ;

Claim 3, line 2, " p(chlorophenyl) " should read - - (p-chlorophenyl) - - ;

Claim 4, line 2, " 2H pyrimi- " should read - - 2H-pyrimi- - - .

Signed and Sealed this

Seventeenth Day of October 1978

[SEAL]

Attest:

RUTH C. MASON
Attesting Officer

DONALD W. BANNER
Commissioner of Patents and Trademarks